(12) United States Patent
Browitt et al.

(10) Patent No.: US 8,778,300 B2
(45) Date of Patent: Jul. 15, 2014

(54) METHOD OF FORMING AN INJECTABLE RADIOACTIVE COMPOSITION OF A CARBON ENCAPSULATED RADIOACTIVE PARTICULATE

(75) Inventors: Rodney James Browitt, Kaleen (AU); Beverley Ann Browitt, legal representative, Kaleen (AU); William Martin Burch, Gymea Bay (AU); Timothy John Senden, Aranda (AU); Ross Wentworth Stephens, Stirling (AU)

(73) Assignee: The Australian National University, Acton (AU)

( * ) Notice: Subject to any disclaimer, the term of this patent is extended or adjusted under 35 U.S.C. 154(b) by 1451 days.

(21) Appl. No.: 11/912,806

(22) PCT Filed: Apr. 28, 2006

(86) PCT No.: PCT/AU2006/000554
§ 371 (c)(1),
(2), (4) Date: Dec. 30, 2008

(87) PCT Pub. No.: WO2006/116798
PCT Pub. Date: Nov. 9, 2006

(65) Prior Publication Data
US 2011/0002847 A1    Jan. 6, 2011

(30) Foreign Application Priority Data
Apr. 29, 2005 (AU) .................. 2005902180

(51) Int. Cl.
*A61K 51/04* (2006.01)
(52) U.S. Cl.
USPC ...................................................... 424/1.65
(58) Field of Classification Search
None
See application file for complete search history.

(56) References Cited

U.S. PATENT DOCUMENTS

| 4,513,607 A * | 4/1985 | Coupal ........................ 73/61.63 |
| 5,064,634 A | 11/1991 | Burch |
| 5,228,444 A | 7/1993 | Burch |
| 5,770,030 A * | 6/1998 | Hamacher et al. .............. 205/43 |
| 5,792,241 A | 8/1998 | Browitt |
| 6,342,598 B1 * | 1/2002 | Anelli et al. .................. 540/474 |
| 6,977,068 B1 | 12/2005 | Nair |

FOREIGN PATENT DOCUMENTS

| WO | WO93/15768 A1 | 8/1993 |
| WO | WO99/04827 A1 | 2/1999 |

OTHER PUBLICATIONS

TechnegasPlus Technegas Generator User Manual, 2005, Vita Medical Limited, title pages and p. 9.*
Lloyd JJ, Shields RA, Taylor CJ, Lawson RS, James JM, Testra HJ. Technegas and Pertechnegas particle size distribution. 1995 Eur. J. Nucl. Med. 22: 473-476.*
Simon BH, Ando HY, Gupta PK. Circulation time and body distribution of 14C-labeled amino-modified polystyrene nanoparticles in mice. 1995 J. Pharm. Sci. 84: 1249-1253.*
Senden, et al. *J. Nuclear Med.* 38:1327-33 (1997).
Moller, W. et al., "A generator for the production of radiolabelled ultrafine carbonaceous particles for deposition and clearance studies in the respiratory tract", Journal of Aerosol Science (2006) 37:631-644.
VITA Medical Newsletter, Issue 1, Jan. 2006, 6 pages.

* cited by examiner

*Primary Examiner* — Michael G Hartley
*Assistant Examiner* — Jennifer Lamberski
(74) *Attorney, Agent, or Firm* — Kilpatrick Townsend & Stockton LLP

(57) ABSTRACT

A method of forming an injectable radioactive composition, the method comprising the steps of: (a) depositing a solid form of technetium onto a carbon crucible; (b) preheating the solid form of technetium to remove any carrier; (c) plasma ablating the technetium and portions of the carbon crucible; (d) allowing the carbon and technetium metal to co-condense from the gas phase to produce a nanoparticle composite aerosol in an inert gas; (e) dispersing the nanoparticle composite in water containing a low concentration of surfactant using an electrostatic precipitator; (f) size fractionating the nanoparticle dispersion by filtration with hydrophilic membranes of known pore size.

12 Claims, 16 Drawing Sheets

METHOD OF FORMING AN INJECTABLE RADIOACTIVE COMPOSITION OF A CARBON ENCAPSULATED RADIOACTIVE PARTICULATE

FIELD OF THE INVENTION

The present invention relates to the methods of production of radioactive isotope compounds (including chemical compounds, or composites and mixtures thereof) and, in particular, discloses methods for the production of injectable radioactive compositions. In one aspect, the present invention relates to methods of production of technetium isotope compounds and injectable radioactive technetium compositions.

BACKGROUND OF THE INVENTION

Methods for production of carbon encapsulated technetium labelled nanoparticle composites are well known. These composites have been found to exhibit avidity for fibrin(ogen) and thus become incorporated in and label fibrin clots. PCT application PCT/AU98/00582 (WO99/04827) (which was also granted on 20 Dec. 2005 as U.S. Pat. No. 6,977,068) discloses a method for use of this property in detecting fibrin clots. Hence, technetium labelled nanoparticle composites have special is value in diagnostic medical imaging and also potential for targeted therapy.

U.S. Pat. No. 5,228,444 to Burch entitled "Device for Producing a Gas-Lite Radionuclide Composition" discloses a method and apparatus for production of such radionuclides. In particular, there is described a carbon crucible heated to a temperature within the range of 1500° to 2500° Celsius. The resulting aerosol product was later found to consist of the nanoparticle composite described by Senden et al (J. Nuclear Med. 38:1327-33, 1997) which also reported on incorporation of other isotopes.

U.S. Pat. No. 5,792,241 to Browitt entitled "Precipitator" discloses a method and apparatus for dispersing the nanoparticle composite into an aqueous medium.

Both of the aforementioned patents are herein incorporated by cross reference.

The process of composite production can therefore proceed as illustrated schematically in FIG. 1 wherein a suitably modified technetium aerosol production device (2) as disclosed in U.S. Pat. No. 5,228,444 is utilised in conjunction with an argon gas source (3) to output an aerosol form of technetium. Subsequently, this is dispersed (5) in water in accordance with the teachings of U.S. Pat. No. 5,792,241. The arrangement of FIG. 1 is further discussed in U.S. Pat. No. 5,792,241.

OBJECT OF THE INVENTION

It is an object of the present invention to provide an improved form of radioactive composite product suitable for use as an injectable agent in diagnostic medical imaging or provide an alternative to the prior art.

SUMMARY OF THE INVENTION

In accordance with a first aspect of the present invention, there is provided a method of forming an injectable radioactive composition of a radioactive particulate, the method including the steps of:
(a) forming a carbon encapsulated nanoparticle composite with a radioactive particulate core in aerosol form; and
(b) dispersing the nanoparticle composite in an aqueous medium comprising a low concentration of surfactant.

The injectable radioactive composition may be pharmaceutically acceptable. injectable radioactive composition may be veterinarilly acceptable when it is intended to be injected into an animal (e.g. a non human mammal). The surfactant may comprise sodium deoxycholate or any other suitable surfactant(s) for intravenous injection. The surfactant may be a pharmaceutically acceptable surfactant.

The method can also include the step of storing the dispersed nanoparticle composite material with a substantially non-electrolyte.

The substantially non-electrolyte can be for example 5% glucose as commonly used in clinical intravenous applications. However, it should be noted that the storage time is limited by isotope decay. The half-life of isotope decay for technetium is only 6.0 hours.

The ionic concentration of the stored dispersion in one embodiment of the present invention should not exceed the equivalent of one millimolar sodium chloride (e.g. it may be 0.25 to 1 millimolar, 0.29 to 0.7 millimolar or 0.3 to 0.5 millimolar). In an example of the present invention, the ionic concentration of the stored nanoparticle composite dispersion is derived from 300 micromolar sodium dihydrogen citrate at a pH of 4.1, with 10 micromolar sodium deoxycholate. The sodium deoxycholate may be in the range of from about 2 to about 100, about 5 to about 50, about 7 to about 20, or about 8 to about 15 micromolar sodium deoxycholate.

The method can also include the step of storing the precipitated material in a low concentration of a buffer solution. The buffer solution may be a weakly acidic buffer solution such as 200 to 400 micromolar sodium dihydrogen citrate or 300 micromolar sodium dihydrogen citrate at pH 4.1.

The step of storing the precipitated material may be in a buffer solution having a suitable pH. The pH may be in the range of about 3.0 to about 7.5, about 3.0 to about 7.0, about 3.5 to about 7.0, about 4.0 to about 7.0, about 4.0 to about 7.0, about 4.0 to about 6.5, about 4.0 to about 6.0, about 4.0 to about 5.5, about 4.0 to about 5.0, or about 4.0 to about 4.5. The pH of the acidic buffer may also be about 3.5, about 4.0, about 4.5, about 5.0, about 5.5, about 6.0, about 6.5, about 6.6, about 6.7, about 6.8, about 6.9, about 7.0, about 7.1, about 7.2, about 7.3, about 7.4, or about 7.5.

The method can also include size fractionation of the nanoparticles by filtration through hydrophilic membranes of known pore size. Suitable filters which may be used in the filtration of the nanoparticles are those hydrophilic membrane filters with nominal cut-offs of about 800 nanometers, about 470 nanometers and about 220 nanometers.

In accordance with a further aspect of the present invention, there is provided a is method of forming an injectable radioactive composition, the method comprising the steps of:
(a) depositing a solid form of a radioactive isotope and a carrier onto a carbon crucible;
(b) preheating the solid form of the radioactive isotope and the carrier to remove the carrier; and
(c) plasma ablating the radioactive particle and portions of the carbon crucible. Step (c) may comprise:
(c) plasma ablating the radioactive particle and portions of the carbon crucible to form a carbon encapsulated nanoparticle composite with a radioactive particulate core in aerosol form. The method may further comprise:
(d) dispersing the nanoparticle composite in an aqueous medium comprising a low concentration of surfactant.

The method may be a method of forming a pharmaceutically or veterinarilly acceptable injectable radioactive composition.

In accordance with a further preferred aspect of the present invention, there is provided a method of forming an injectable radioactive composition, the method comprising the steps of:
(a) depositing a solid form of technetium and a carrier onto a carbon crucible;
(b) preheating the solid form of technetium and the carrier to remove the carrier; and
(c) plasma ablating the technetium and portions of the carbon crucible. Step (c) may comprise:
(c) plasma ablating the technetium and portions of the carbon crucible to form a carbon encapsulated nanoparticle composite with a radioactive technetium particulate core in aerosol form.

The method may further comprise:
(d) dispersing the nanoparticle composite in an aqueous medium comprising a low concentration of surfactant.

The method of the invention may be a method of forming a pharmaceutically or veterinarilly acceptable injectable radioactive composition.

The solid form of technetium may be sodium pertechnate or any insoluble form of technetium produced during the electrolytic process as described herein, e.g. insoluble oxichlorides. The technetium may be in the form of a radioactive isotope of technetium.

An example of a radioactive isotope of the present invention is technetium, specifically $^{99m}Tc$, but this is not exclusive, as shown by Senden et al (above) and the incorporation of other radioisotopes or radionuclides can be utilised. Other suitable radioactive isotopes include $^{67}Ga$, $^{68}Ga$, $^{113m}In$, or $^{111}In$. $^{198}Au$, $^{64}Cu$, $^{213}Bi$, $^{57}Co$, $^{51}Cr$, $^{165}Dy$, $^{169}Er$, $^{59}Fe$, $^{67}Ga$, $^{68}Ga$, $^{153}Gd$, $^{166}Ho$, $^{111}In$, $^{113m}In$, $^{177}Lu$, $^{23}Na$, $^{24}Na$, $^{103}Pd$, $^{81}Rb$, $^{82}Rb$, $^{186}Re$, $^{188}Re$, $^{75}Se$, $^{153}Sm$, $^{117m}Sn$, $^{89}Sr$, $^{201}Th$, $^{90}Y$, $^{169}Yb$.

The step (a) of the further aspect of the present invention may also include an electrolytic concentration of the radioisotope with the carbon crucible acting as a cathode of an electrolytic cell and an anode which may comprise a platinum wire placed in a cavity formed by said crucible.

The absolute chemical concentration of Tc isotope eluted from a molybdenum decay generator is of the order of picomolar. Thus in common usage concentrations of isotope are quoted as radioactivity, in this case in the millicurie range. The Tc loading may be in the range of from about 1 to about 100 mCi (or from about 0.2 to about 4 GBq).

The Tc loading may also be in the range of from about 1 to about 100 mCi, about 5 to about 100 mCi, about 7.5 to about 95 mCi, about 10 to about 90 mCi, about 15 to about 85 mCi, about 20 to about 80 mCi, about 25 to about 75 mCi, about 30 to about 70 mCi, about 35 to about 65 mCi, about 40 to about 60 mCi, about 45 to about 55 mCi, or about 50 to about 55 mCi.

The preheating step (b) may be at a sufficient temperature to evaporate the carrier, for example sodium chloride, but insufficient to remove the radionuclide or radioisotope, for example a technetium compound. The preheating step (b) may be at a temperature substantially in the range of about 1200° to about 1800° C., about 1250° to about 1800° C., about 1300° to about 1800° C., about 1350° to about 1800° C., about 1400° to about 1750° C., about 1450° to about 1750° C., about 1500° to about 1700° C., about 1550° to about 1700° C., about 1600° to about 1700° C., and about 1650° C. to about 1700° C.

The preheating step (b) may be conducted over a period of time in the range from about 0.1 to about 1000 seconds, from about 0.1 to about 900 seconds, from about 0.2 to about 800 seconds, from about 0.3 to about 700 seconds, from about 0.4 to about 600 seconds, from about 0.5 to about 500 seconds, from about 0.6 to about 400 seconds, from about 0.7 to about 350, from about 0.8 to about 300 seconds, from about 0.9 to about 250, from about 1.0 to about 200 seconds, from about 1.1 to about 150 seconds, from about 1.2 to about 100 seconds, from about 1.3 to about 95 seconds, from about 1.4 to about 90 seconds, from about 1.5 to about 85 seconds, from about 1.6 to about 80 seconds, from about 1.7 to about 75 seconds, from about 1.8 to about 70 seconds, from about 1.9 to about 65 seconds, from about 2.0 to about 60 seconds, from about 2.1 to about 55 seconds, from about 2.2 to about 50 seconds, from about 2.3 to about 45 seconds, from about 2.4 to about 40 seconds, from about 2.5 to about 35 seconds, from about 2.5 to about 30 seconds, from about 2.5 to about 25 seconds, from about 5.0 to about 25 seconds, from about 5.0 to about 20 seconds, from about 7.5 to about 20 seconds, from about 10.0 to about 20 seconds, from about 12.5 to about 20 seconds, from about 12.5 to about 17.5 seconds, from about 12.5 to about 15.0 seconds, from about 15.0 to about 17.5 seconds, or about 15.0 seconds.

The preheating step (b) may be conducted over a period of time in the range from about substantially 1 to 50 seconds, 2.5 to 45 seconds, 5 to 40 seconds, 5 to 35 seconds, 5 to 30 seconds, 5 to 25 seconds, 10 to 20 seconds, 12.5 to 17.5 seconds, 15 to 17.5 seconds, 12.5 to 15.0 or about 15 seconds where the carrier is sodium chloride.

The preheating temperature can be substantially at the boiling point of the carrier. The preheating temperature may be in the range 1300 to 17 50° C., 1400 to 1750° C., 1500 to 1750° C., 1600 to 1700° C., or substantially at about 1685° C., where the carrier is, for example, sodium chloride.

The time taken to reach the effective preheating temperature from ambient conditions (rise-time) may be from about 0.1 to about 5 seconds, about 0.15 to about 4.5 second, about 0.2 to about 4.0 seconds, about 0.25 to about 3.5 seconds, about 0.30 to about 3.0 seconds, about 0.35 to about 3.0 seconds, about 0.40 to about 2.5 seconds, about 0.4 to about 2.0 seconds, about 0.4 to about 1.5 seconds, about 0.45 to about 1.5 seconds, about 0.5 to about 1.5 seconds, and from about 0.75 to about 1.5 seconds and from about 1.0 to about 1.5 seconds. The rise-time may be substantially 1 second, 1.1 seconds, 1.15 seconds, 1.2 seconds, 1.25 seconds, 1.3 seconds, 1.35 seconds, 1.4 seconds, 1.45 seconds, or 1.5 seconds.

The method can be operated in an atmosphere of an inert gas or inert atmosphere. The inert gas or inert atmosphere may comprise argon, neon, helium, or a mixture thereof. The inert gas or inert atmosphere may be argon, helium, or a mixture thereof and preferably may be an argon atmosphere.

The plasma ablation step (c) can occur at a temperature in the range of from about 2000° C. to about 3000° C., about 2100° C. to about 3000° C., about 2200° C. to about 2900° C., about 2300° C. to about 2900° C., about 2400° C. to about 2900° C., about 2500° C. to about 2900° C., about 2600° C. to about 2900° C., about 2700° C. to 2900° C., about 2700° C. to 2800° C., about 2700° C. to 2800° C., and about 2740° C. to 2790° C. The ablation may preferably occur at approximately 2765° C.

The period of time for the plasma ablation step (c) may be from about 1.0 to 5.0 seconds, 1.5 to about 4.5 seconds, 2.0 to about 4.0 seconds, and about 2.5 to about 3.5 seconds. The time taken to reach the effective ablation temperature may be from about 0.1 to about 0.5 seconds, 0.2 to about 0.4 seconds or about 0.3 seconds.

The method may also comprise a step (d) of precipitating the ablated particles in a sonicating electrostatic precipitator. The method may also comprise the step of: (d) precipitating the aerosol product in a sonicating electrostatic precipitator. The precipitator preferably may include pure water with a low concentration of a suitable surfactant. The surfactant can comprise sodium deoxycholate, but may be any surfactant suitable for injection.

The method can also include the step of: storing the precipitated material as an aqueous dispersion with addition of a substantially non-electrolyte. Preferably the dispersion is stored in a low concentration of a weakly acidic buffer e.g. 300 micromolar sodium dihydrogen citrate at a pH of 4.1. The level of soluble pertechnetate anion present as a contaminant in the product can be used as a quality measure. Thin Layer Chromatography (TLC) can be used to determine the percentage of soluble pertechnetate with respect to the total radioactivity (soluble plus particulate) in the product.

BRIEF DESCRIPTION OF THE DRAWINGS

Preferred forms of the present invention will now be described with reference to the accompanying drawings in which.

DESCRIPTION OF PREFERRED AND OTHER EMBODIMENTS

In a preferred embodiment of the present invention, there is provided an improved method of production of radioactive isotope composites such as technetium composites having improved characteristics suitable for diagnostic medical imaging by gamma scintigraphy, and by implication therapy through the encapsulation of other isotopes.

An example of a suitable technetium composite for the present invention is disclosed in PCT/AU98/00582 (WO99/04827). Technegas is an agent that consists of a plurality of discrete particles, each comprising a plurality of coating layers of carbon (varying between two and ten atoms in thickness) which completely enclose a minute crystal of $^{99m}$Tc metal. The particles are stable inert hydrophobic particles having a diameter of 10 to 500 nanometers. FibrinLite comprises an aqueous dispersion of these particles, which may be size-fractionated by hydrophilic membrane filters of nominal cut-off values, e.g. 800 nm, 470 nm and 220 nm. The particles can be sedimented by high-speed centrifugation and redispersed by agitation, thus enabling a convenient separation or purification process. The particles in a FibrinLite dispersion aggregate on addition of electrolytes (see FIGS. 9, 10 and 11), thus enabling complete separation by filtration.

Figure 2:
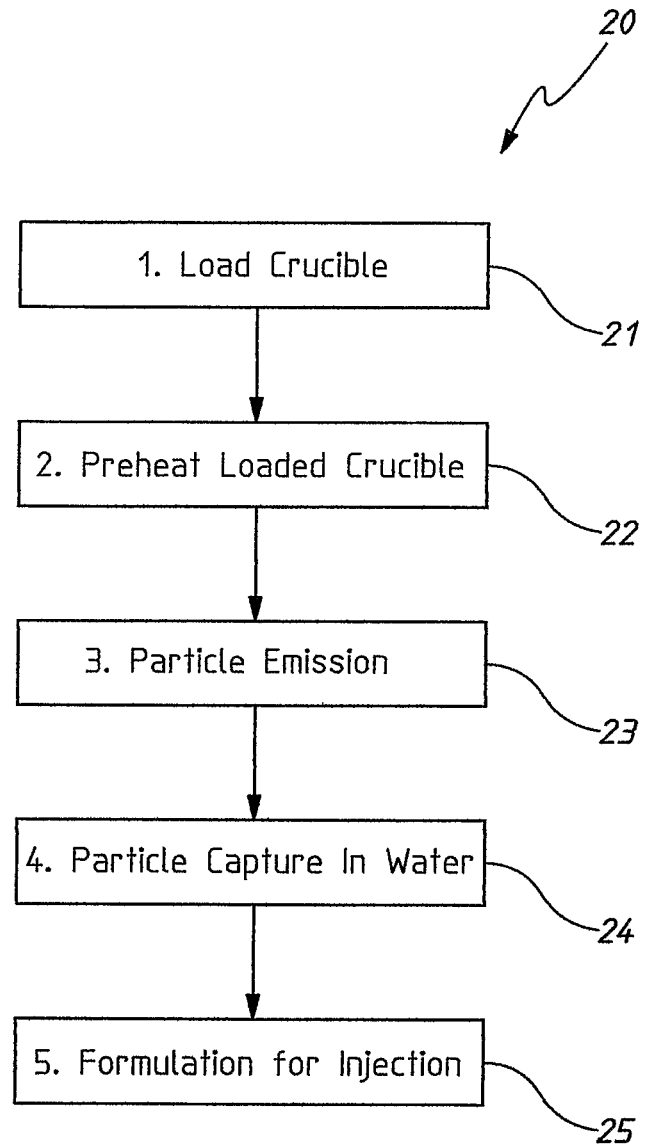
FIG. 2 illustrates the steps involved in an embodiment of a method in accordance with the present invention.

The steps of the preferred embodiment of the method of the present invention can be as illustrated in FIG. 2. The method 20 can include an initial step of loading a crucible with technetium 21, preheating the loaded crucible 22, flash emission of the Technegas particles 23, particle capture in water 24 and formulation for injection 25. Each of these steps is discussed in further detail hereinafter. The purity and size of the nanoparticles produced were found to be strongly dependent on the production conditions employed.

Step 1: Crucible Loading (21)

Figure 3:
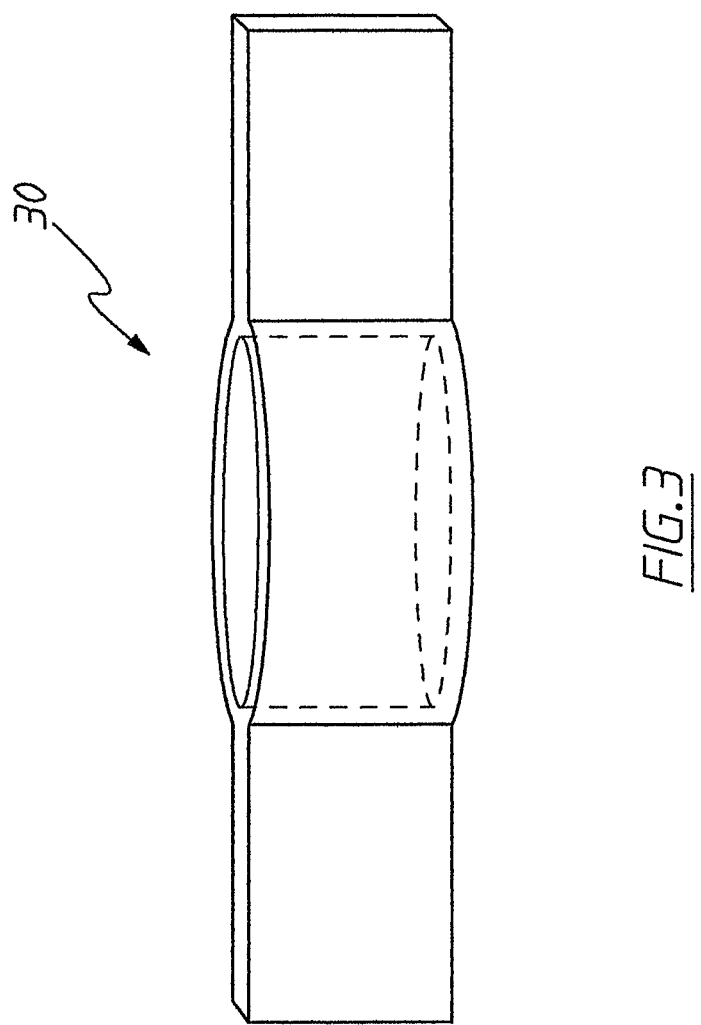
FIG. 3 illustrates an enlarged view of a crucible utilised in a method of the present invention.

A technetium isotope is commercially available as sodium pertechnetate eluted with saline from the alumina matrix of a molybdenum-decay generator. FIG. 3 illustrates a crucible 30 of the type disclosed in U.S. Pat. No. 5,228,444 suitable for loading. The disclosure of U.S. Pat. No. 5,228,444 is incorporated herein by cross-reference.

The technetium isotope in saline solution may be used to load a suitable graphite crucible by two methods:

Evaporative Method:

If the technetium generator eluate has sufficient specific activity, eg, 100 mCi/mL, then the crucible 30 may be loaded simply by placing 100 microlitres of generator eluate in the crucible 30 and evaporating the saline solution to dryness by carefully regulated resistive heating of the crucible 30. This technique is disclosed in U.S. Pat. No. 5,228,444.

Electrolytic Concentrator Method:

This method enables the isotope to be sourced from technetium generators having low eluate activity. The nanoparticles produced from this method were found to have a lower level of pertechnetate contamination (eg, <5%) than the evaporative method defined in U.S. Pat. No. 5,228,444.

Figure 4:
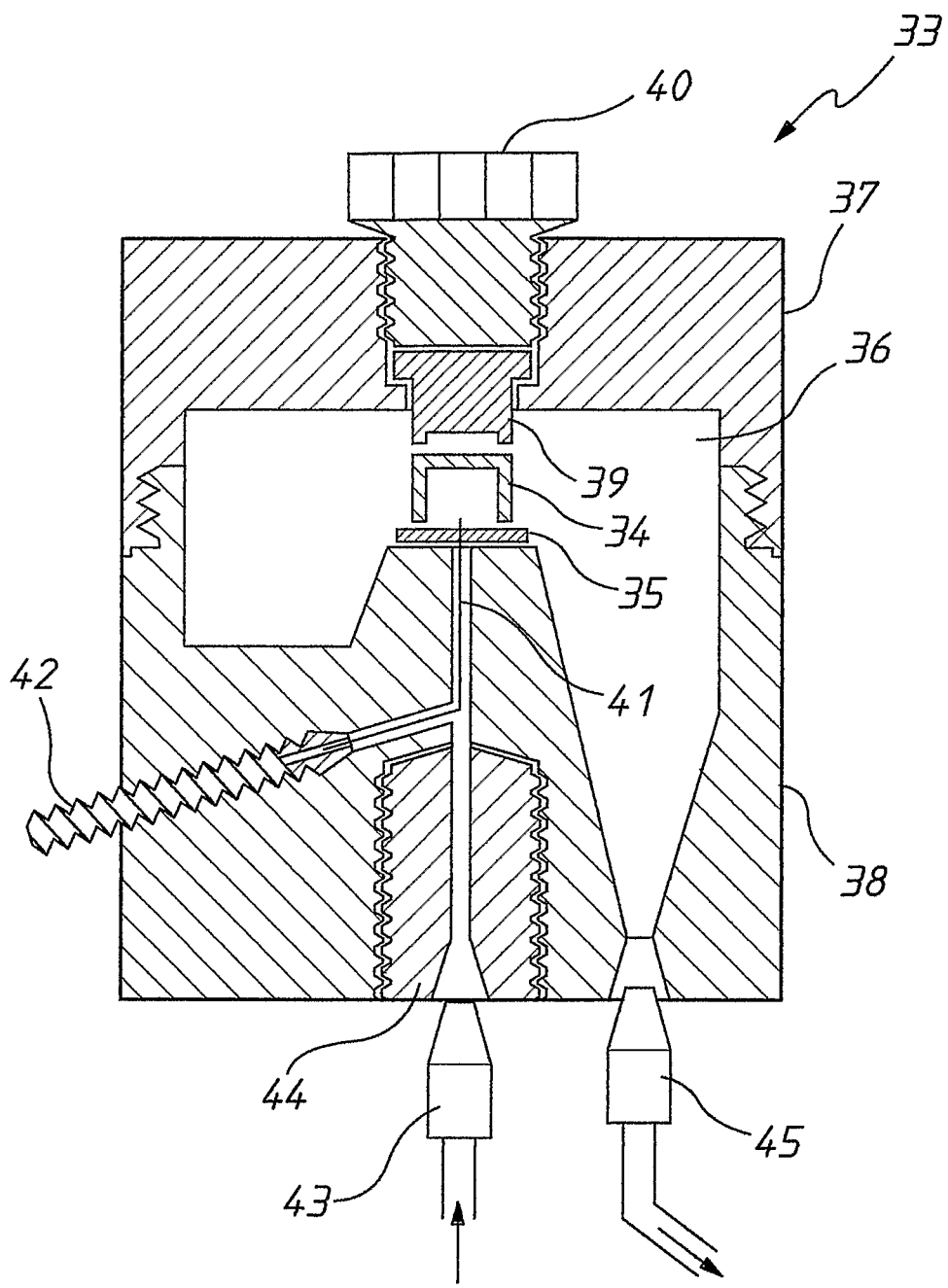
FIG. 4 is a sectional view of a first electrolytic concentrator utilised in a method of the present invention.

FIG. 4 is a sectional view of a first embodiment of an electrolytic concentrator 33 used in a method of the present invention. A crucible 34 forms a cathode of the electrolytic concentrator 33 and is placed on a silicone rubber gasket 35 inside a chamber 36 formed from two mating parts 37, 38. The crucible 34 is held in place by means of a stopper 39 and a pressure adjusting screw 40. The anode of the cell consists of a fine platinum wire 41 which runs up the centre of the fluid delivery tube. The fluid delivery tube is in communication with a Luer tapered liquid input tube 43 via a polycarbonate insert 44. The anode is connected to the power supply through the screw insert 42. The saline isotope solution is pumped into the chamber 36 and exits via Luer output taper 45 to a reservoir (not shown) where it is recirculated. The outer shell 37, 38 can be formed from Teflon or Teflon coated materials.

Figure 4B:
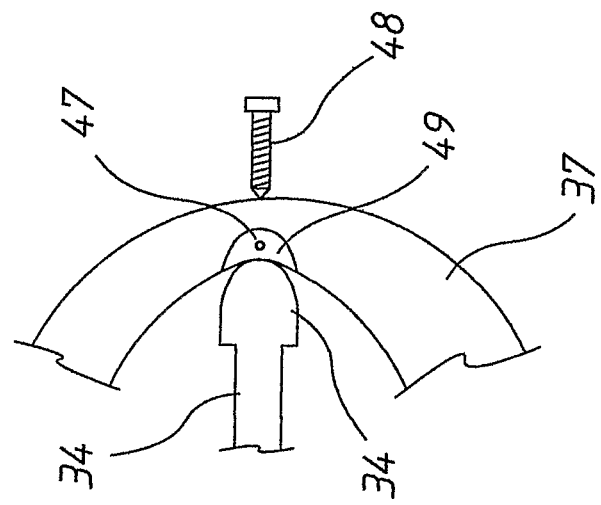
FIG. 4a and FIG. 4b illustrate in more detail the interconnection of the crucible to the cathode in the electrolytic concentrator shown in FIG. 4.
Figure 4A:
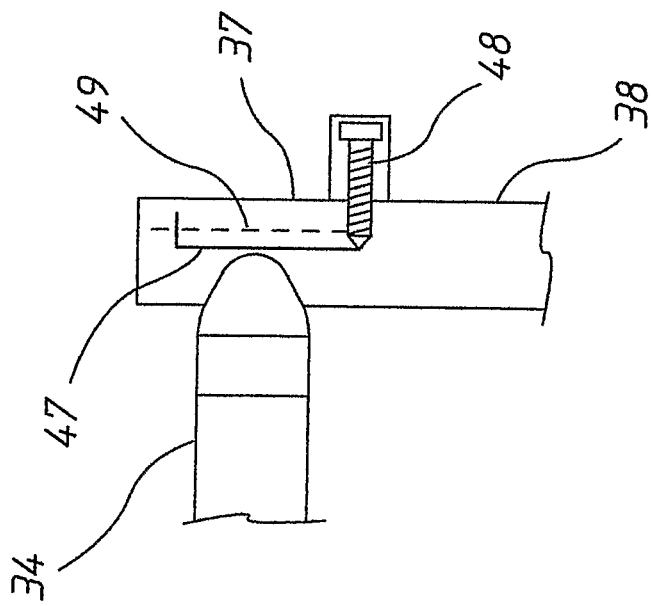

FIG. 4a and FIG. 4b illustrate the formation of the crucible cathode in more detail with FIG. 4a illustrating a side view and FIG. 4b illustrating a top view. The crucible 34 is interconnected to a platinum wire contact 47 which is held in place against the crucible 34 by silicone rubber 49. The wire is attached to a contact screw 48 which forms the negative power supply input.

Utilising the disclosed arrangement as an electrolytic concentrator, the isotope of technetium was found to be concentrated onto the inner surface of a graphite crucible by the combined action of the electrolysis and the continuous pumping. The operating specifications can be shown in the following Table I below:

TABLE I

| Process Component | Parameter | Range | Preferred Value |
|---|---|---|---|
| Concentrator loading of graphite crucible | Ethanol addition to saline | 15-40% | 30% |
| | Electrolyte flow transiting crucible walls | 0.1-0.7 mL/min | 0.33 mL/min |
| | Constant current through electrolytic cell | 1-10 mA | 5 mA |
| | Duration of electrolysis | 10-60 min | 30 min |

The saline eluate from a technetium generator is circulated continuously through the walls of a porous graphite crucible 34 under the pressure of a peristaltic pump. The crucible 34 forms the cathode of an electrolytic cell and the anode consists of the fine platinum wire 41 placed in the opening of the crucible 34. Radionuclide is deposited on the graphite surface inside the crucible opening. The accumulation of radionuclide in the crucible 34 may be conveniently monitored by the loss of radioactivity from the circulating liquid, eg, with a Geiger counter placed over a few loops of the tubing circuit or adjacent to the fluid reservoir.

The second embodiment of an electrolytic concentrator 33a is similar to the first embodiment of the electrolytic concentrator 33 except for the provision of an outlet tube 50 which allows for the flow of saline out of the crucible 34. The same reference numerals as for the first embodiment of the electrolytic concentrator will be used to is denote the same or similar items of the second embodiment of the electrolytic concentrator 33a.

The electrolytic concentrator 33a enables production of FibrinLite with a level of pertechnetate contamination that is uniformly lower than that found in preparations made with the first embodiment of the electrolytic concentrator 33. This is especially important for FibrinLite production, since some additional pertechnetate is released from the nanoparticles during sterilization by autoclaving. FibrinLite produced using the second embodiment of the electrolytic concentrator crucible loading releases less free pertechnetate on autoclaving; and thus it is believed that the nanoparticles have greater heat stability.

The superior results produced by the second embodiment of the electrolytic concentrator loading are attributable to a particular conditioning process for the crucible surface. The surface conditioning of the crucible 34 is achieved in the concentrator 33a by an electrolytic process prior to loading with a radionuclide.

The use of an electrolytic concentrator 33, 33a has already been documented as providing three useful features in the production of both TechneGas and FibrinLite:
1) The electrolytic concentration of radionuclide in the carbon crucible allows the use of considerably weaker sources of technetium isotope, both from molybdenum-decay generators that are weaker sources to begin with, and also generators that are weaker due to age.
2) The electrolytic concentration of radionuclide is selective, in that it does not result in concentration of the carrier sodium chloride in the crucible. By contrast, the concentration of radionuclide in crucibles by multiple evaporative loadings concentrates sodium chloride to such an extent that the encrustation of salt interferes with proper crucible function.
3) The electrolytic loading of the carbon crucible produces TechneGas and FibrinLite with lower contamination by free non-encapsulated pertechnetate.

The second embodiment of the electrolytic concentrator offers a further reduction in pertechnetate contamination of FibrinLite, which is particularly noticeable after autoclaving.

Figure 14:
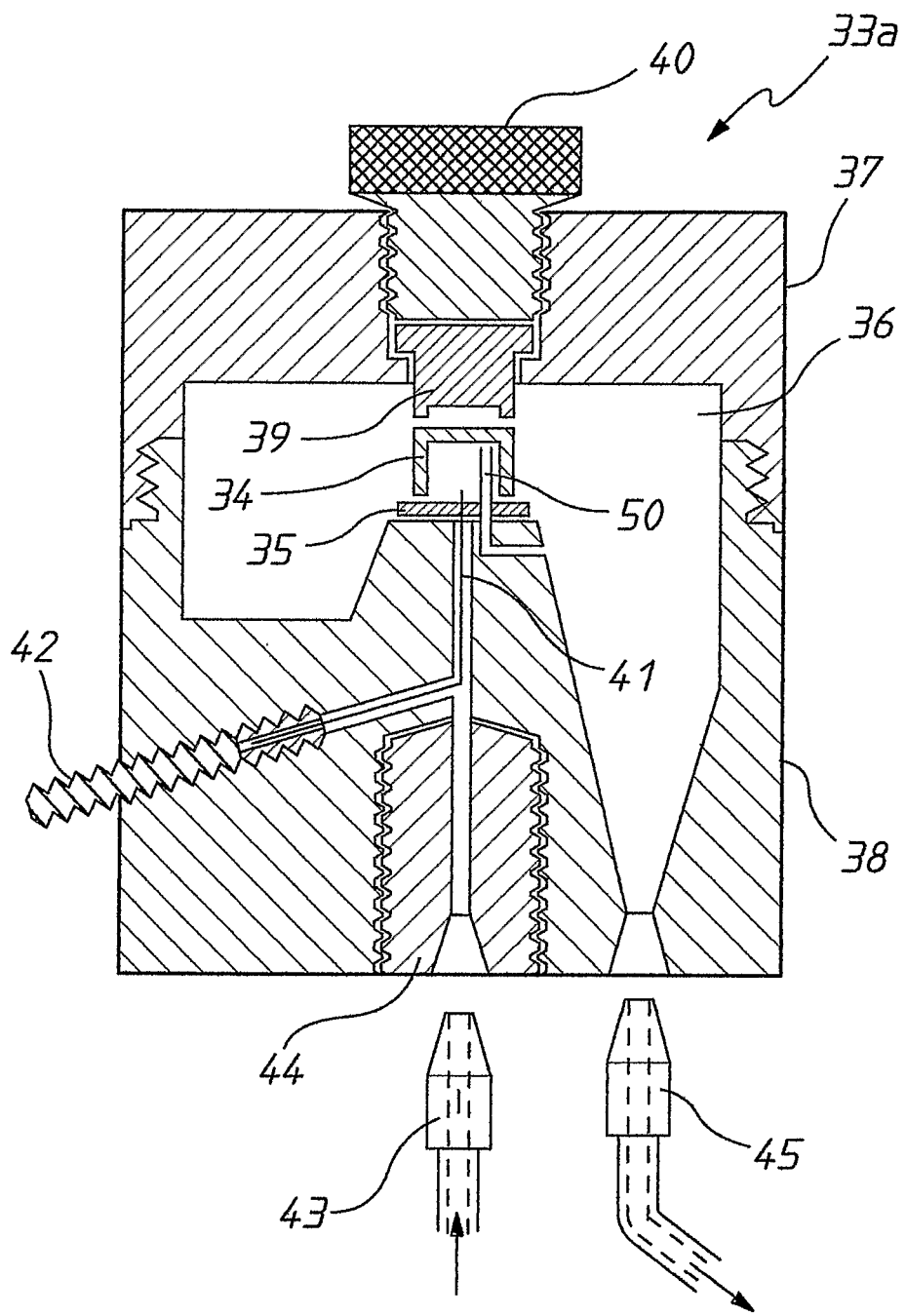
FIG. 14 illustrates a sectional view of a second electrolytic concentrator utilised in another method of the present invention.

The flow cell for the second embodiment of the electrolytic concentrator 33a is shown in FIG. 14. The electrolytic concentrator 33a comprises an inverted carbon crucible 34 located over a centrally positioned platinum needle wire electrode 41, as also shown in the first embodiment of the electrolytic concentrator 33 (See FIG. 4). However in the second embodiment of the electrolytic concentrator 33a, a fine outlet tube 50 is positioned inside a crucible cavity which is defined by the inverted carbon crucible 41 and the silicone rubber gasket 35, such that a first end of the tube 50 is located just under the upper portion of the crucible cavity and a second end is located beneath the base of the crucible cavity. In use, fluid exits from the crucible cavity from just beneath the roof or upper portion of the crucible cavity and flows through the silicone rubber gasket 35 to exit at the second end thereof into the chamber 36. This enables higher flow rates of fluid through the cell without the requirement for forced transit through the crucible's porous graphite walls, as required in the first embodiment of the electrolytic concentrator 33 as shown in FIG. 4.

The second embodiment of the electrolytic concentrator 33a of the present invention enables production of FibrinLite with a level of pertechnetate contamination that is uniformly lower than that found in preparations made with the first embodiment of the electrolytic concentrator 33. This is especially important for FibrinLite production, since some additional pertechnetate is released from the nanoparticles during sterilization by autoclaving. FibrinLite produced using crucible loading of the second embodiment of the electrolytic concentrator 33a releases results in less free pertechnetate on autoclaving; and thus it is believed that the nanoparticles have greater heat stability.

The superior results produced by the crucible loading of the second embodiment of the electrolytic concentrator 33a are attributable to a particular conditioning process for the surface of the crucible 34. The surface conditioning of the crucible 34 is achieved in the electrolytic concentrator 33a by an electrolytic process prior to loading with the radionuclide.

The second embodiment of the electrolytic concentrator 33a enables the use of higher current densities, as required for crucible surface conditioning, by allowing faster saline flow rates through the cell. In the first embodiment of the electrolytic concentrator 33, the concentrator fast flow rates are not obtainable due to the requirement for saline to exit through the porous graphite walls of the crucible 34. The saline outlet tube 50 should be positioned close to but not touching the roof or upper portion of the cell (i.e. the base of the inverted crucible), and should be made of a non-conducting, heat-resistant polymer.

Before loading, the surface of the crucible 34 is first treated electrolytically in the second embodiment of the electrolytic concentrator 33a, in such a manner that the graphite surface of the crucible 34 is conditioned to provide a larger effective area of carbon for deposition of a radionuclide. To achieve this effect, a dual power supply (not shown) is provided, which is capable of supplying both a pulsed heavy current for crucible conditioning, as well as a constant low current for loading of radionuclide (see Table II. Similarly, a peristaltic pump is provided, capable of pumping fluid through the cell at a high rate during pulsed current crucible conditioning, as well as a slow rate during radionuclide loading (see Table II).

Since the crucible conditioning treatment produces considerable heat, a cooling airflow is provided over the outer surface of the crucible surface. Air is drawn through the chamber of the concentrator by a small electric pump.

Suitable conditions for crucible conditioning and loading are shown in Table II below.

TABLE II

| Parameter | Preferred Value | Allowable Range |
|---|---|---|
| Crucible Conditioning | | |
| Duration | 30 mins | 25-45 mins |
| Pulse Height | 600 mA | 500-750 mA |
| Pulse Width | 1.5 milliseconds | 1.0-2.0 milliseconds |
| Saline Volume | 2.5 mL | 1.5-3.5 mL |
| Saline flow rate | 70 mL/hour | 50-90 mL/hour |
| Crucible Loading | | |
| Duration | 45 min | 30-50 min |
| Constant Current | 80 mA | 50-100 mA |
| Fluid Volume | 2.5 mL | 1.5-3.5 mL |
| Fluid flow rate | 5 mL/hour | 3-8 mL/hour |

Full Description of Operation

Conditioning and Loading of the crucible is done in three steps;

1. Hydrocarbon treatment of the crucible to make the internal space of the graphite matrix hydrophobic and thus reduce saline transit through the body of the crucible during loading.
2. Electrolytic conditioning to enlarge the effective surface area of the graphite.
3. Electrolytic loading of isotope onto the surface of the crucible cavity.

The first two steps can be done at least two or three days before the crucible is required.

Hydrocarbon Treatment

1) Fill the crucible with 125 microlitres of a solution of paraffin oil in "petroleum ether" (e.g. 50 microlitres of paraffin oil per 100 mL of pet ether).
2) Carefully "dry" the crucible with air updraft 10 cm above a hot plate.

Electrolytic Conditioning

1) Place the crucible upside down between the two openings in the rim of the concentrator, so that the crucible cavity is positioned over the sealing disk. The cavity is positioned over the inlet and the outlet for saline flow, and the platinum anode that is concentric with the saline inlet. One end of the crucible makes electrical contact with a platinum wire in an opening of the Teflon rim.
2) Carefully locate the lid of the concentrator over the rim, screw it down and then gently tighten the central white pressure screw that presses the crucible cavity walls into the sealing disk.
3) Introduce 3.0 mL saline into the pump circuit through a T-junction using a syringe. Start the peristaltic pump and adjust so that the saline circulates at 70 mL per hour.
4) Start the aircooling for the crucible by switching on the airpump, which draws air through the concentrator chamber.
5) Turn on the pulsed DC power supply and adjust the peak current to 600 mA.
6) Set the timer going for 30 mins. On expiry stop current and both pumps, disassemble.

Electrolytic Loading of Isotope

1) Make up the charge fluid with saline Tc99m eluate (80%) and ethanol (20%), to give a volume of e.g. 2.5 mL. Measure the radioactivity using a dose calibrator.
2) Assemble the conditioned crucible and lid on the concentrator as above.
3) Introduce the isotope solution into the pump circuit with a shielded syringe, connected through the T-valve. Adjust the flow rate to 5 mL per hour.
4) Turn on the airflow pump to draw cooling air through the concentrator chamber.
5) Turn on the constant current DC power supply and adjust to 80 mA.
6) Set the timer for 45 min. On expiry, turn off the power supply, the peristaltic pump and the airflow pump. Disassemble and measure the radioactivity of the loaded crucible, using a dose calibrator.

Results

Figure 15:
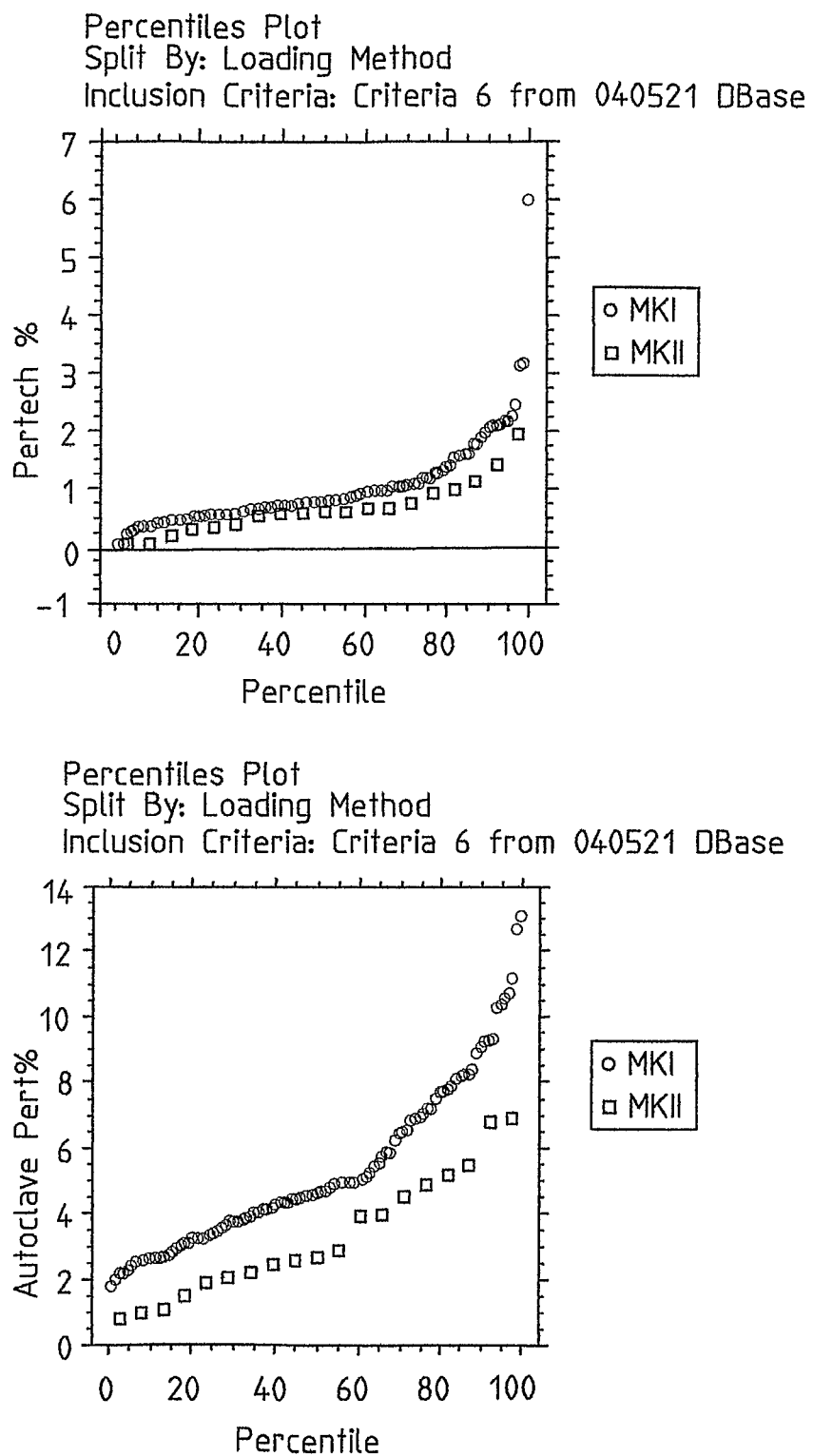
FIG. 15 shows two graphs of the results of 105 FibrinLite preparations using the first embodiment of the electrolytic concentrator as shown in FIGS. 4 and 19 preparations using the second embodiment of the electrolytic concentrator as shown in FIG. 14.

The results for 105 FibrinLite preparations using the first embodiment of the electrolytic concentrator ('MkI concentrator conditions') and 19 preparations using the second embodiment of the electrolytic concentrator ('MkII concentrator conditions') are shown in two graphs in FIG. 15.

In particular, FIG. 15 shows the pertechnetate contamination of FibrinLite preparations before (upper graph) and after (lower graph) autoclaving, with MkI and MkII concentrator crucible loading conditions.

The pertechnetate contamination in FibrinLite precipitator fluid is shown in the upper percentiles graph in FIG. 15, and the pertechnetate contamination in autoclaved FibrinLite is shown in the lower graph in FIG. 15.

The MkI concentrator conditions using the first embodiment of the electrolytic concentrator produced FibrinLite precipitator fluid with a median of 0.82% (interquartile range (IQR) of 0.61% to 1.2%) pertechnetate contamination.

The MkII concentrator conditions using the second embodiment of the electrolytic concentrator produced a median of 0.63% (IQR of 0.4% to 0.9%). A Mann-Whitney test showed that there was a significant reduction in pertechnetate contamination using MkII conditions ($p=0.019$).

This difference was considerably larger when pertechnetate contamination was measured in FibrinLite after autoclaving. Autoclaved FibrinLite produced using MkI concentrator conditions showed a median pertechnetate contamination of 4.6% (IQR 3.35% to 6.93%), while for autoclaved MkII FibrinLite the median was only 2.63% (IQR 1.93% to 4.71%). A Mann-Whitney test showed that there was a highly significant reduction in pertechnetate contamination in autoclaved FibrinLite made using MkII concentrator conditions ($p=0.0008$).

Step 2: Preheating of the Loaded Crucible (22)

It has surprisingly been found that a carefully controlled preheating step after crucible loading and prior to particle generation has a marked effect on the nature of the nanoparticles subsequently plasma ablated from the crucible at a higher temperature and is therefore considered an important step. During the preheating step, a carrier, for example sodium chloride is removed, preferably by evaporation into a flow of inert gas, for example. argon. and at a suitable temperature and for a predetermined time. The conditions outlined in the following Table III were found to be suitable for sodium chloride. For other carriers, the protocol can be followed with suitable variation of the rise time and the temperature. The boiling point of the carrier must be lower than the temperature range which will lead to loss of isotope from the crucible.

TABLE III

| | Variable | Range | Preferred Value |
|---|---|---|---|
| Pre-heating of crucible and removal of salt | Argon purge of crucible chamber - flow rate | 6-14 liters/min | 8 liters/min |
| | Argon purge of crucible chamber - duration | 3-10 min | 6 min |
| | Crucible temperature rise time from ambient to evaporation temperature, eg 1685° C. | 0.5-1.5 sec | 1.25 sec |
| | Temperature for sodium chloride evaporation from crucible | 1200-1800° C. | 1685° C. |
| | Duration of sodium chloride evaporation from crucible | 5-25 sec | 15 sec |

Suitable conditions are given in Table III, namely 1685° C. for 15 seconds. The sodium chloride evaporation by crucible heating and inert gas purging is preferably carried out in a suitably modified device of the type which has previously been disclosed in U.S. Pat. No. 5,064,634, which has been previously incorporated herein by cross-reference.

Specifically, it was not previously appreciated that the duration of the preheating step affects:

1. Carbon emission from the crucible during plasma ablation.

A step of preheating the crucible for at least 5 seconds at a temperature above the boiling point of sodium chloride (eg, 1685° C.) but below the temperature used to induce thermionic plasma (eg, 2750° C.) was found to markedly reduce the amount of free carbon subsequently ablated from the crucible. A suitable preheating step results in an aqueous nanoparticle dispersion that is almost optically clear, and facilitates filtration to obtain nanoparticle fractions of known size ranges suitable for use as an injectable product.

2. Pertechnetate contamination levels of the nanoparticle dispersion.

Figure 5:
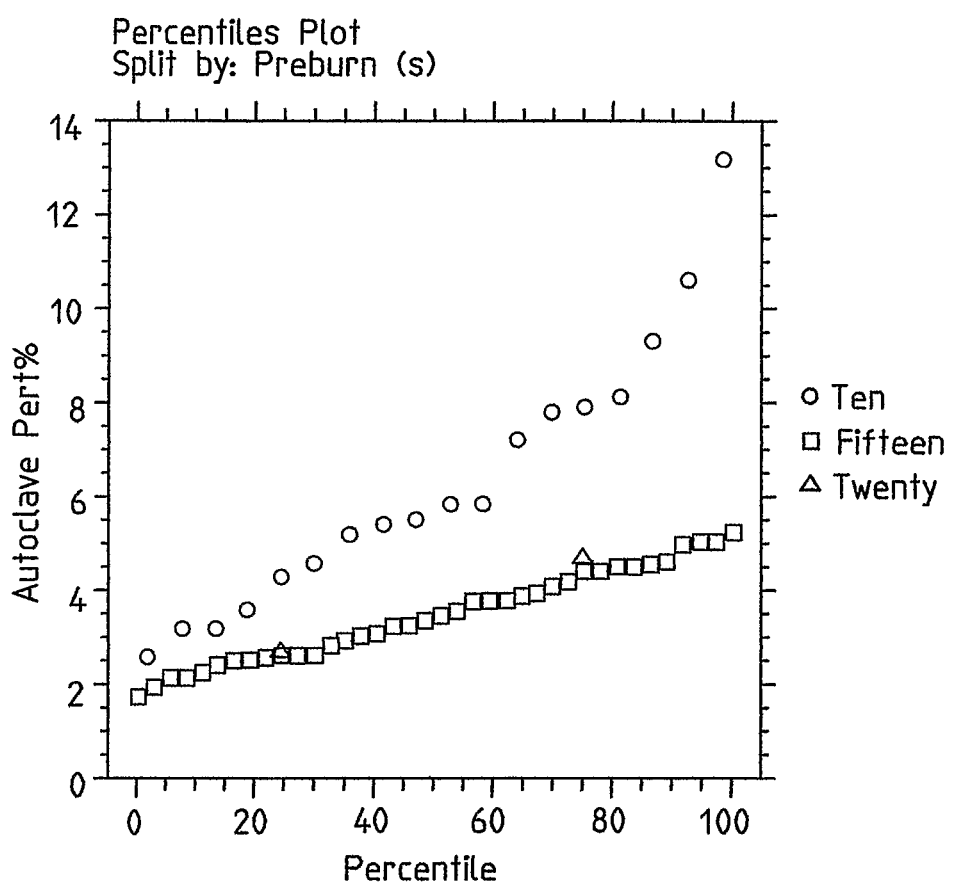
FIG. 5 is a graph illustrating the results of crucible preheating in terms of liberated pertechnetate percentage found after autoclaving of the dispersion.

A step of preheating the crucible for at least 5 seconds also produces a significant reduction in the level of water-soluble pertechnetate label contaminating the nanoparticle dispersion. It was found that nanoparticles produced after sufficient preheating of the crucible have a greater stability to heat sterilization, i.e., less free pertechnetate label is released into the solution from these nanoparticle suspensions during autoclaving. FIG. 5 illustrates a graph of various curves of different duration of preheating and the effect of duration of crucible preheating on the level of pertechnetate contamination of the final nanoparticle dispersion after autoclaving. While there is a range of free pertechnetate contamination after the preparations from different crucibles are autoclaved, this range diminishes with increased preheating times, up to periods of 15 seconds.

3. Size of nanoparticles produced.

Figure 6:
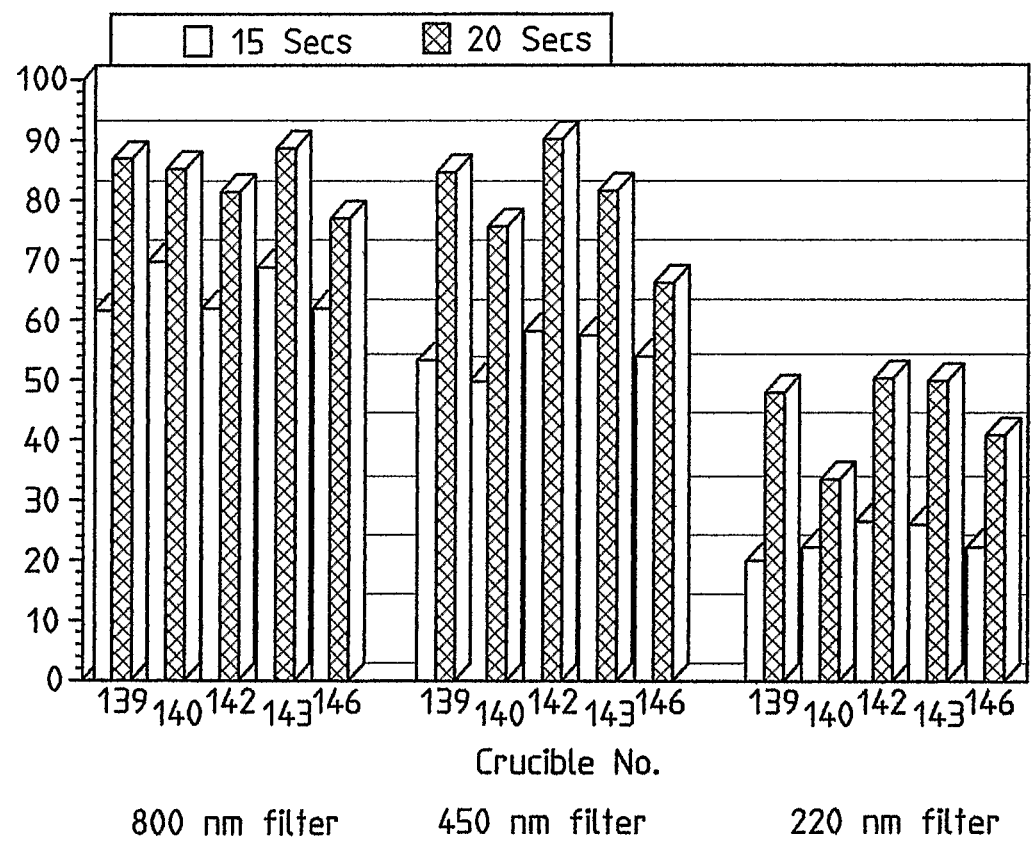
FIG. 6 is a graph illustrating the results of crucible preheating on the size of nanoparticles produced.

It was found that prolonged preheating of the crucible for, eg, 20 seconds, increases the proportion of radiolabel that is present in smaller particle fractions, specifically below 450 nm. FIG. 6 illustrates resulting graphs showing the effect of duration of crucible preheating on the size of nanoparticles produced, measured as the percentage of radioactivity that passes though hydrophilic membrane filters having cut-off values as shown. Distributions of radiolabel are shown 60-62 in three filter fractions from nanoparticle preparations produced independently from five different crucibles, using preheating steps of 15 and 20 seconds.

Step 3: Particle Production (25)

Figure 7:
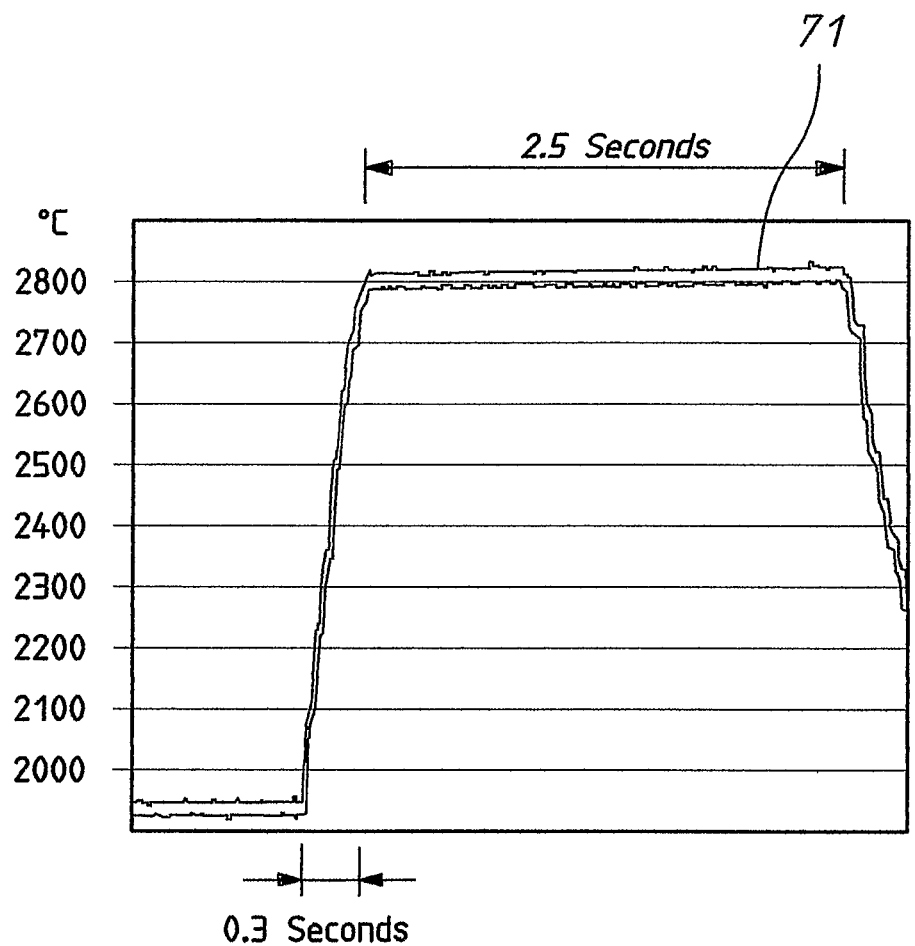
FIG. 7 illustrates the heating profile for ablation.

The pretreated crucible from step 2 was flash-heated in accordance with the heating profile set out in FIG. 7 to 2740-2790° C. (71) for 3 seconds by means of an electronic servo device, which produced a tightly-regulated crucible heating profile featuring a rapid rise time 72 (eg, 0.3 seconds) followed by a flat plateau 71 maintaining, eg, 2765° C.±15° C. over the predetermined heating period. These conditions can be produced by modifying the electronic controller of the device of U.S. Pat. No. 5,064,634. The heating regime of the preferred embodiment differs from that of U.S. Pat. No. 5,064,634 in that U.S. Pat. No. 5,064,634 mentions briefly only resistive heating to 2200° C. of a carbon crucible containing a solid radionuclide, whereas the preferred embodiment includes preheating the crucible and carrier removal prior to nanoparticle emission and that the temperature during thermionic plasma induction and particle ablation is tightly maintained in a considerably higher temperature range as indicated in the following Table IV of desirable conditions:

TABLE IV

| Process Component | Parameter | Range | Preferred Value |
|---|---|---|---|
| Plasma ablation | Crucible temperature rise time for plasma ignition | 0.3-0.7 secs | 0.4 secs |
| | Crucible temperature for plasma ablation | 2700-2800° C. | 2765° C. |
| | Duration of plasma ablation | 2.5-3.5 secs | 3.2 secs |

FIG. 7 shows an actual thermoprofile for regulated AC plasma ablation of a graphite crucible at 2800° C. for 2.5 seconds. Note the rapid rise-time 72 (0.3 seconds) to full ablation temperature.

The temperature was measured using a calibrated optical pyrometer.

Step 4: Particle Capture in Water (24)

Figure 1:
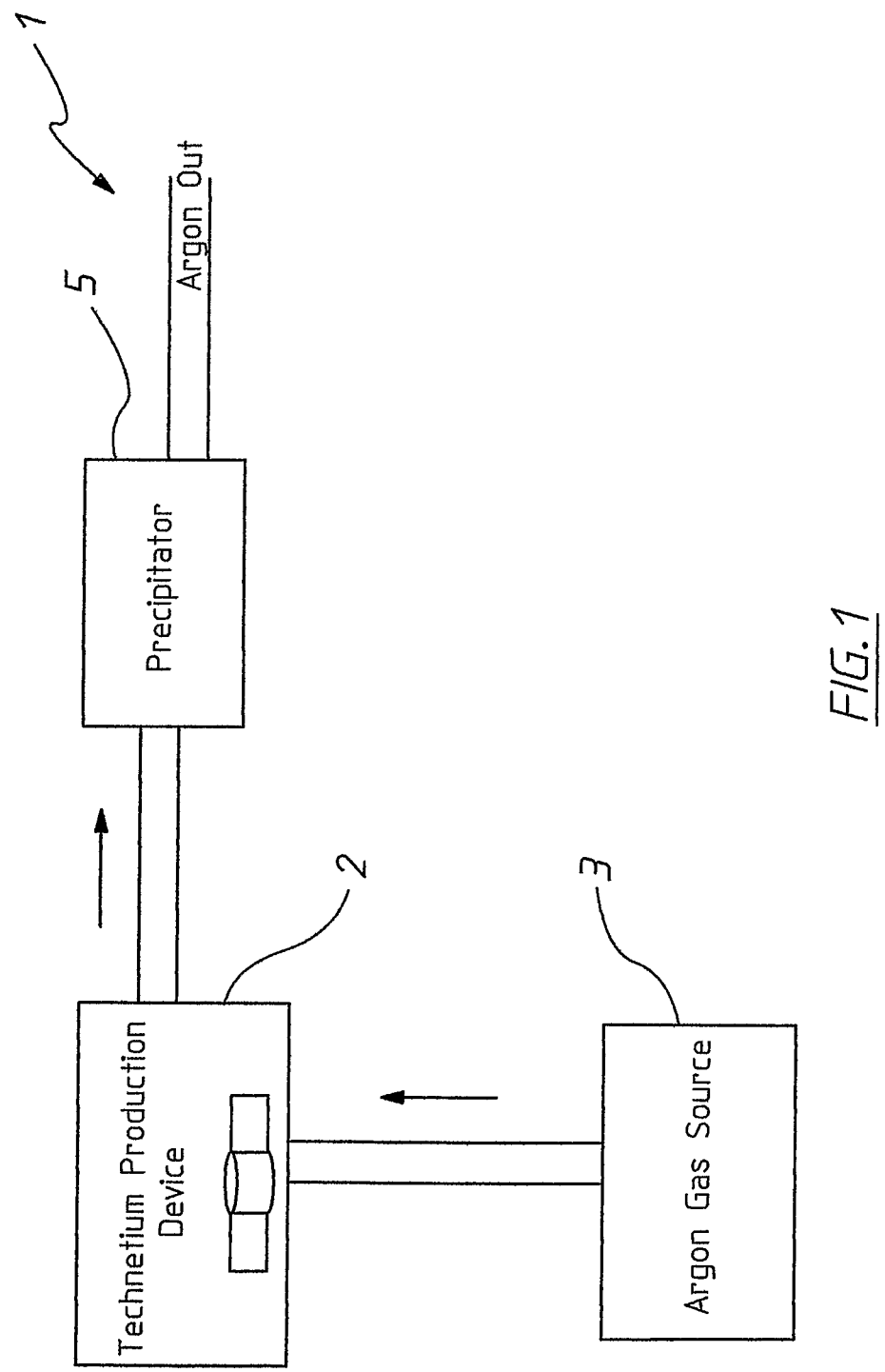
FIG. 1 illustrates a process 1 of composite production comprising technetium in accordance with the present invention.
Figure 8:
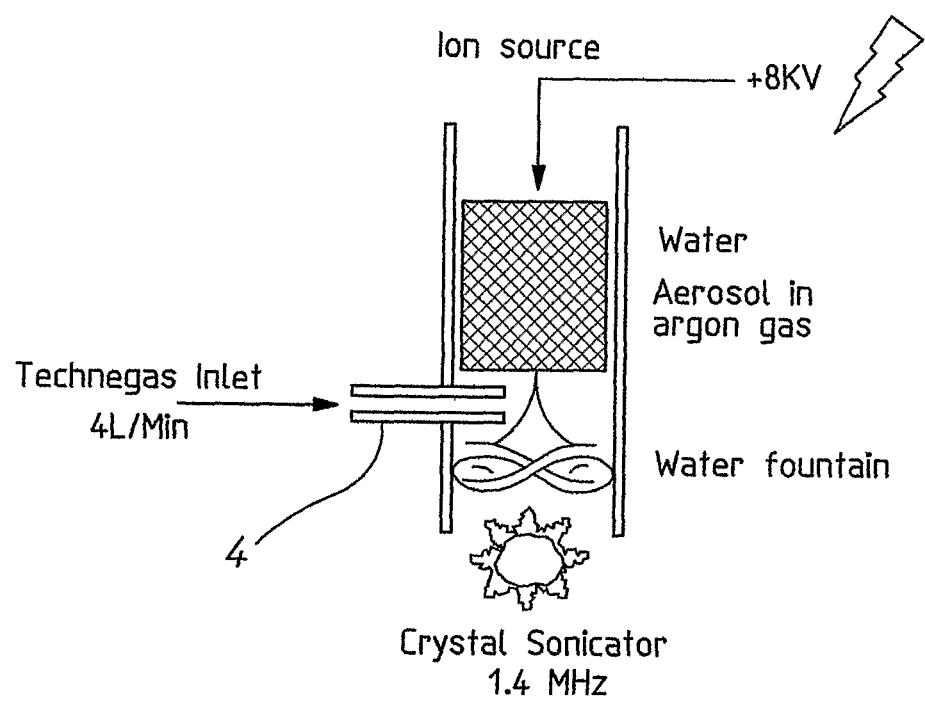
FIG. 8 illustrates schematically a precipitator utilised in a method of the present invention.

As illustrated in FIG. 1, the vapour particles emitted from the flash-heated crucible 2 are immediately carried off in an argon stream 4 to a sonicating electrostatic precipitator 5 charged with pure water containing only a very low concentration of a surfactant, eg, 10 micromolar sodium deoxycholate. Note that this surfactant is approved of by the US Food and Drug Administration (FDA) for use in intravenous injections. The precipitator can be as disclosed in U.S. Pat. No. 5,792,241 and is shown schematically in FIG. 8.

The precipitator can be operated in accordance with the following Table V:

TABLE V

| | Variable | Range | Preferred Value |
|---|---|---|---|
| Precipitator conditions for collection of particles | High tension applied to platinum needle ion source (anode) | 5-10 kV and limited to 15 µA current | 8 kV sustained at 8 µA leakage |
| | Sonicator crystal frequency | 1.4-1.7 MHz | 1.7 MHz |
| | Sonicator power level | 10-40 W | 20 W |
| | Argon flow through precipitator | 3-6 L/min | 4 L/min |
| | Water volume | 2.0-3.0 mL | 2.8 mL |
| | Surfactant concentration, eg, sodium deoxycholate | 2-20 µM | 10 µM |

This type of precipitator can be used to disperse nanoparticles emitted from the crucible in a stable aqueous dispersion. A surfactant may be added to the water to increase suspension stability, but only very low ionic strength conditions (eg, less than 100 micromolar) should be employed. Other surfactants could be employed if they are suitable for intravenous injection of humans. The dispersion is pharmaceutically acceptable (particularly when used for humans) or may be veterinarily acceptable if it is intended for injection into an animal.

Step 5: Formulation of Nanoparticles for Injection (25)

Figure 9:
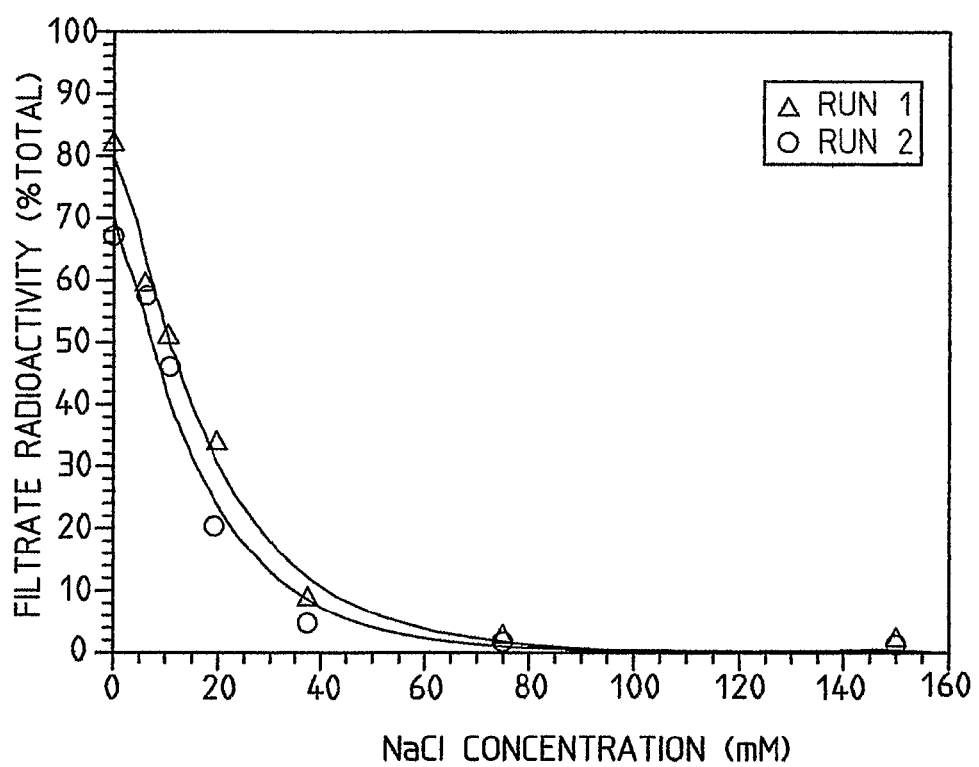
FIG. 9 illustrates the effect of sodium chloride concentrations on the resulting nanoparticle dispersion product.
Figure 10:
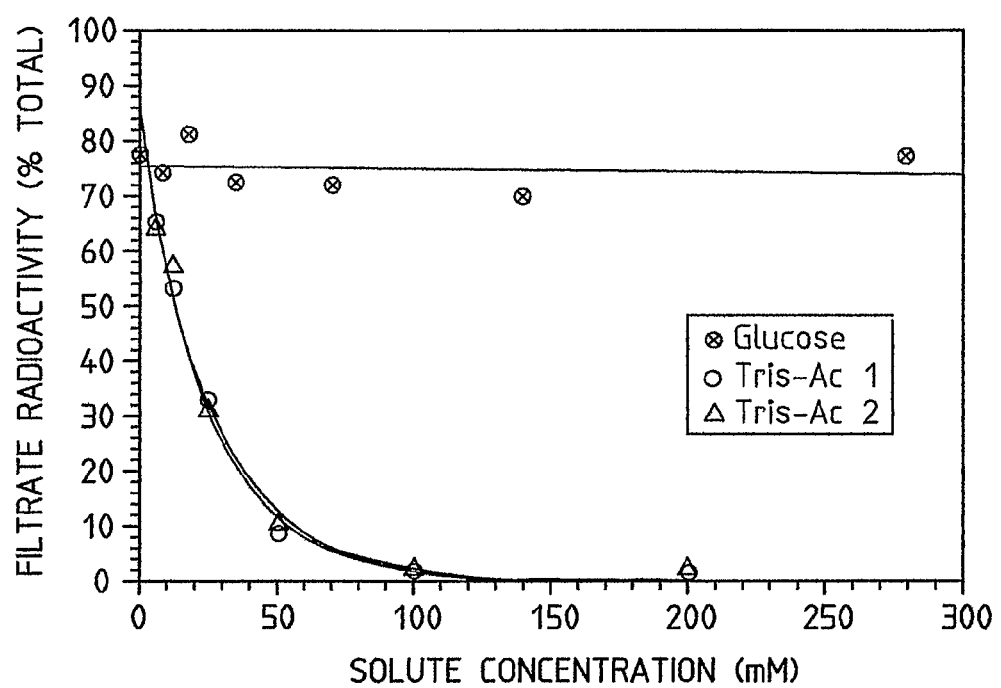
FIG. 10 illustrates the effect of tris-acetate and glucose concentrations on the resulting nanoparticle dispersion product.
Figure 11:
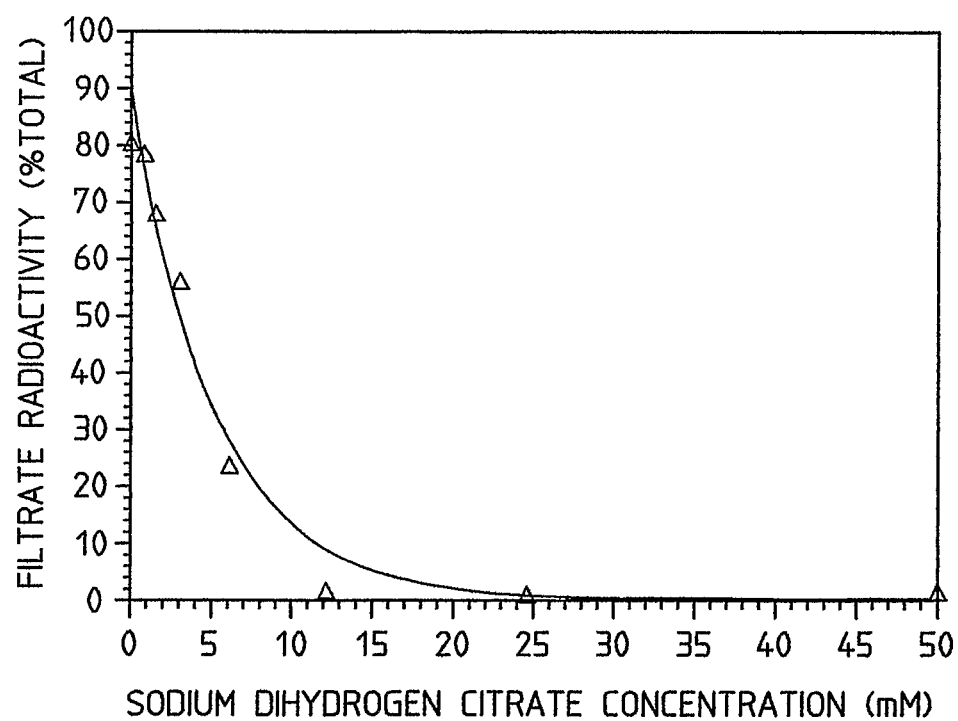
FIG. 11 illustrates the effect of sodium dihydrogen citrate concentration on the resulting nanoparticle dispersion product.

It was found that the stability of the final nanoparticle dispersion in water is dependent upon ionic strength and pH. Addition of electrolytes to nanoparticles to final concentrations greater than a few millimolar results in rapid aggregation of nanoparticles, as evidenced by a marked increase in retention of radiolabel by a 450 nm hydrophilic membrane filter. Example results are shown in FIG. 9 to FIG. 11 with FIG. 9 showing the effect of sodium chloride concentration on mixed cellulose ester (MCE) membrane filtration of nanoparticles, using a filter with a nominal cut-off of 450 nm, FIG. 10 shows the effect of Tris-acetate and glucose concentration on MCE membrane filtration of nanoparticles and FIG. 11 shows the effect of sodium dihydrogen citrate concentration on MCE membrane filtration of nanoparticles. Addition of non-electrolytes, eg, glucose, does not induce aggregation and thus may be used to provide an iso-osmolar formulation for intravenous injection if desired.

It was also found that the integrity of the nanoparticles was dependent on maintaining a slightly acidic pH, eg, pH 4.0. This was found to be particularly important during autoclaving in order to minimise release of free pertechnetate. FIG. 10 shows the levels of free pertechnetate contamination that were found after autoclaving nanoparticles preparations at pH 4.0 and pH 10. The figure shows the effect of pH on the stability of nanoparticles during 20 minutes autoclaving at 121° C. measured as release of free pertechnetate (TLC method). The values of free pertechnetate are shown in the percentiles graph for unautoclaved particles (Pertech %), autoclaved particles (Autoclave Pert %) particles autoclaved with pH 4.0 buffer (P % Autocl pH 4.0) and particles autoclaved with pH 10.0 buffer (P % Autocl pH 10.0).

Thus a preferred method of formulation for nanoparticles is to add a very low concentration of a weakly acidic buffer to the nanoparticle dispersion immediately after collection from the precipitator, eg, a final concentration of 300 micromolar sodium dihydrogen citrate at pH 4.1.

FIG. 6 illustrates the particle size distribution of radioactivity in nanoparticle preparations made using five different crucibles and with preheating duration of 15 seconds and 20 seconds. The fractions were obtained using hydrophilic MCE membrane filters. Note that a higher proportion of radioactivity passes through the filters when nanoparticles are produced after preheating of loaded crucibles for 20 seconds. The majority of radioactivity is present in particles less than 450 nm in diameter, and it is preferred that this fraction be used as the routine formulation of nanoparticles for intravenous injection.

Quality Control for the Nanoparticle Product

Figure 12:
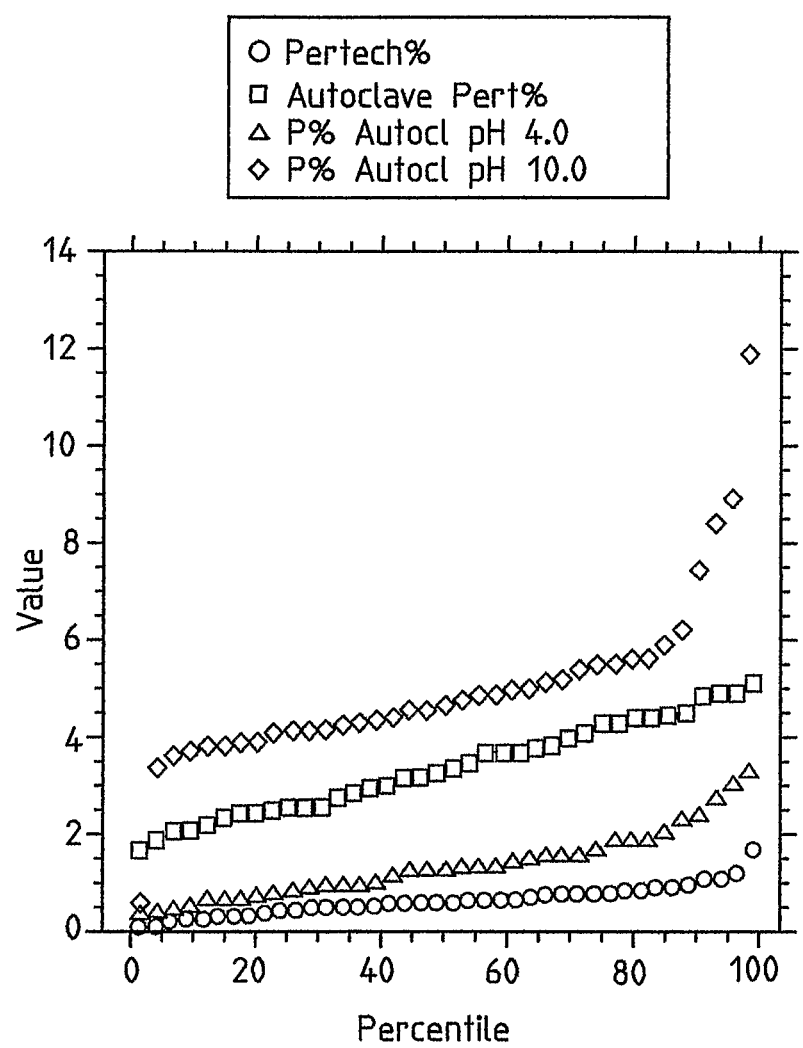
FIG. 12 illustrates the effect of pH on nanoparticle stability during autoclaving.
Figure 13:
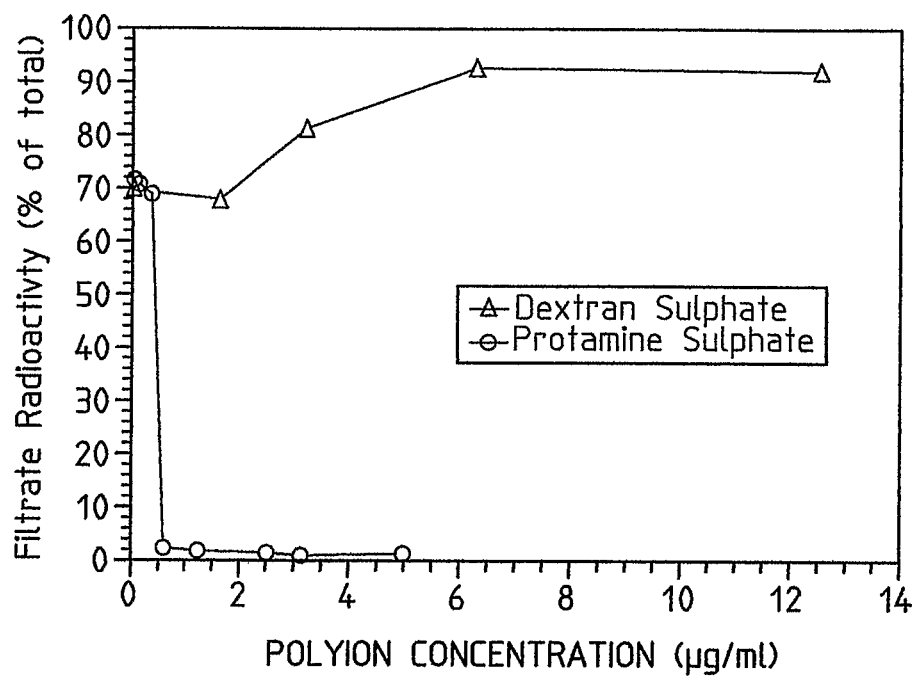
FIG. 13 illustrates the effect of polyions on the nanoparticle dispersion product.

The level of pertechnetate contamination in nanoparticle preparations is conveniently and rapidly measured by thin-layer chromatography (TLC) using silica gel as the stationary phase and, eg, methylethyl ketone (MEK) or normal physiological saline is as the mobile phase. The radioactivity remaining at the origin provides a measure of immobile radioactivity present in particles, while the migration front radioactivity gives a measure of free pertechnetate that can be expressed as a percentage of the total radioactivity applied to the TLC. Typical values for pertechnetate contamination in precipitator fluid and autoclaved nanoparticles are <1.5% and <5% respectively as illustrated in FIG. 12.

However, not only free pertechnetate, but also hydrolysable species, such as technetium carbide, may be contaminants of the nanoparticle aerosols and dispersions. Thus the difference between free pertechnetate present in nanoparticle dispersions after autoclaving at pH 4.0 and autoclaving at pH 10.0 is a useful measure of hydrolysable isotope-labelled contaminants. The total level of non-nanoparticle species, such as pertechnetate, should be less than 7% of the total radioactivity.

Size Fractionation by Hydrophilic Membrane Filters

Nanoparticle suspensions formulated with a suitable surfactant, eg, 10 micromolar sodium deoxycholate, may be filtered through syringe filters comprising hydrophilic membranes made of, eg, mixed cellulose ester (MCE) and having known pore sizes, eg, 450 nm.

The majority of radioactivity present in formulated nanoparticles should pass through a 450 nm syringe filter of the MCE type. The proportion of radiolabel passing through this membrane is related to the duration of the crucible preheating step.

Stability of FibrinLite Dispersions—Additions of Solutes

Addition of electrolytes to the nanoparticles causes partial neutralisation of particle charge and aggregation of the nanoparticles, evident as a marked increase in retention of radiolabel by hydrophilic membrane filters. Thus, when the nanoparticles are dilutes in physiological saline (150 mM sodium chloride), the radioactive particles can be virtually quantitatively removed by a 450 nm membrane filter as shown in FIG. 6. Only 7-10 mM sodium chloride is necessary to cause 50% retention by this porosity filter. Similar effects were seen with Tris-acetate (pH 7.5; 50% retention at 15 mM; FIG. 10) and acid citrate (pH 4.0; 50% retention at 3 mM: FIG. 11) buffers, whereas a non-electrolyte, eg, glucose, could be added up to an iso-osmolar concentration, ie, 5%, without causing significant aggregation of the nanoparticles (FIG. 10). The nanoparticles are not aggregated by sodium deoxycholate at concentrations up to 1 mM, ie, 100 times the concentration chosen for routine use as a surfactant in the precipitator (data not shown).

The addition of polyions to nanoparticles reveals a marked difference in response depending on the charge of the polyion. If the nanoparticles are treated with a soluble polycation such as protamine sulphate, the particles are quantitatively aggregated and removed by a 450 rim filter, even at very low protamine concentrations, eg, 0.4 micrograms per mL. This is probably due to bridging of the nanoparticles by the polycation. On the contrary, if the nanoparticles are treated with a soluble polyanion such as dextran sulphate, then retention of the radioactive particles by a 450 nm filter is not increased, even at relatively high concentrations of the polyanion, eg, 100 micrograms per mL.

The foregoing describes preferred forms of the present invention. It is to be understood that the present invention should not be restricted to the particular embodiment(s) shown above. Modifications and variations, obvious to those skilled in the art can be made thereto without departing from the scope of the present invention.

The claims defining the invention are as follows:

1. A method of forming an injectable radioactive composition, the method comprising the steps of:
   (a) depositing a solid form of a radioactive isotope and carrier onto a carbon crucible;
   (b) preheating the solid form of radioactive isotope and carrier to selectively remove the carrier without removal of the radioactive isotope; wherein said preheating is at a preheating temperature in the range of about 1200 to about 1800 degrees Celsius for about 5 to 25 seconds; and wherein said preheating has a rise time from ambient to said preheating temperature of about 0.1 to about 5 seconds;
   (c) plasma ablating the radioactive isotope and portions of the carbon crucible, thereby forming radioactive particles;
   (d) precipitating the ablated radioactive particles in a sonicating electrostatic precipitator;
   (e) maintaining the precipitated radioactive particles in an aqueous dispersion; and,
   (f) size fractionating the precipitated radioactive particles using filtration through hydrophilic membranes of a known pore size;
   thereby forming an injectable radioactive composition.

2. The method as claimed in claim 1, wherein said radioactive particles comprise technetium.

3. The method as claimed in claim 1, wherein said carrier comprises sodium chloride.

4. The method as claimed in claim 1, wherein said preheating is at about 1685 degrees Celsius.

5. The method as claimed in claim 1, wherein said preheating is at a preheating temperature of about 1685 degrees Celsius, and said rise time of said preheating from ambient to said preheating temperature occurs within 0.4 to 1.5 seconds.

6. The method as claimed in claim 5, wherein said rise time is about 1.25 seconds.

7. The method as claimed in claim 1, wherein said method is operated in an argon atmosphere.

8. The method as claimed in claim 1, wherein said plasma ablation occurs at a temperature in the range of from about 2740 to about 2790 degrees Celsius.

9. The method as claimed in claim 8, wherein said ablation occurs at approximately 2765 degrees Celsius.

10. The method as claimed in claim 1, wherein said plasma ablation is for about 2.5 to 3.5 seconds.

11. The method as claimed in claim 1, wherein said precipitator includes water with a low concentration of surfactant.

12. The method as claimed in claim 1, further comprising storing the precipitated material in a low concentrate of weakly acidic buffer.

* * * * *